United States Patent
Mishra et al.

(10) Patent No.: US 7,090,971 B2
(45) Date of Patent: Aug. 15, 2006

(54) TRANSGLUTAMINASE HAS INTRINSIC KINASE ACTIVITY

(76) Inventors: Suresh Mishra, 631 Drake Centre, Winnipeg, Manitoba (CA) R3T 5V4; Liam J. Murphy, 631 Drake Centre, Winnipeg, Manitoba (CA) R3T 5V4

( * ) Notice: Subject to any disclaimer, the term of this patent is extended or adjusted under 35 U.S.C. 154(b) by 0 days.

(21) Appl. No.: 11/040,095

(22) Filed: Jan. 24, 2005

(65) Prior Publication Data
US 2005/0208612 A1 Sep. 22, 2005

Related U.S. Application Data

(60) Provisional application No. 60/539,594, filed on Jan. 29, 2004.

(51) Int. Cl.
*C12Q 1/00* (2006.01)
(52) U.S. Cl. .......................................... 435/4
(58) Field of Classification Search ................... 435/4
See application file for complete search history.

(56) References Cited

OTHER PUBLICATIONS

Fesus et al. TRANSGLUTAMINASE 2: An Enigmatic Enzyme With Diverse Functions; Trends in Biochemical Sciences, vol. 27, No. 10 (2002) pp. 534-539.*
Coverley et al. The Effect of Phosphorylation By Casein Kinase 2 on the Activity Of Insulin-Like Growth Factor-Binding Protein-3; Endocrinology, vol. 141, No. 2 (2000) pp. 564-570.*
Coverley et al. Phorphorylation Of Insulin-Like Growth Factor Binding Proteins; Mol. and Cell. Endocrinology, vol. 128 (1997) pp. 1-5.*
Pattison et al. Insulin-Like Growth Factor Binding Protein-3 is Secreted as a Phosphoprotein by Human Breast Cancer Cells; Mol. and Cell. Endocrinology, vol. 156 (1999) pp. 131-139.*
Sakai et al. Tissue Transglutaminase Facilitates the Polymerization of Insulin-Like Growth Factor Binding Protein-1 (IGFBP-1) and Leads to the Loss of IGFBP-1's Ability To Inhibit Insulin-Like Growth Factor-1-Stimulated Protein Synthesis.*
Continued: The Journal of Biological Chemistry, vol. 276, No. 12, (2001) pp. -8740-8745.*

* cited by examiner

*Primary Examiner*—Patricia Leith
*Assistant Examiner*—Paul C. Martin
(74) *Attorney, Agent, or Firm*—Michael R. Williams; Adrian D. Battison; Ryan W. Dupuis

(57) ABSTRACT

A method of identifying compounds capable of modulating trans-glutaminase (TG) kinase activity is described. The method involves adding a test compound to a mixture of TG and a suitable TG kinase substrate, incubating the mixture under conditions promoting TG kinase activity, and determining if the test compound activates or modulates TG kinase activity as indicated by greater than expected TG-mediated phosphorylation of the TG kinase substrate or if the test compound inhibits TG kinase activity as indicated by lower than expected TG-mediated phosphorylation of the TG kinase substrate as compared to a control comprising TG and a suitable TG kinase substrate incubated under conditions promoting TG kinase activity.

1 Claim, 5 Drawing Sheets

Phosphorylation of retinoblastoma protein and p53 oncoprotein by tissue transglutaminase

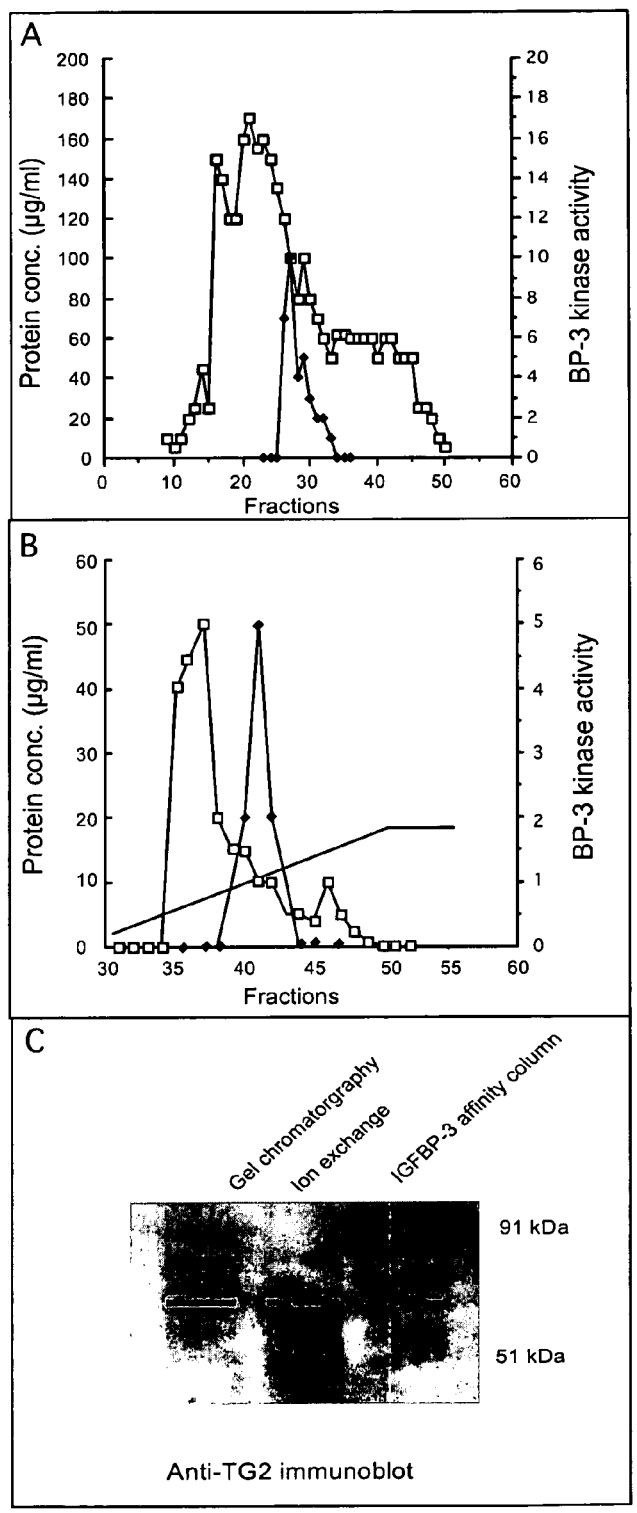
Fig. 1 Mishra & Murphy

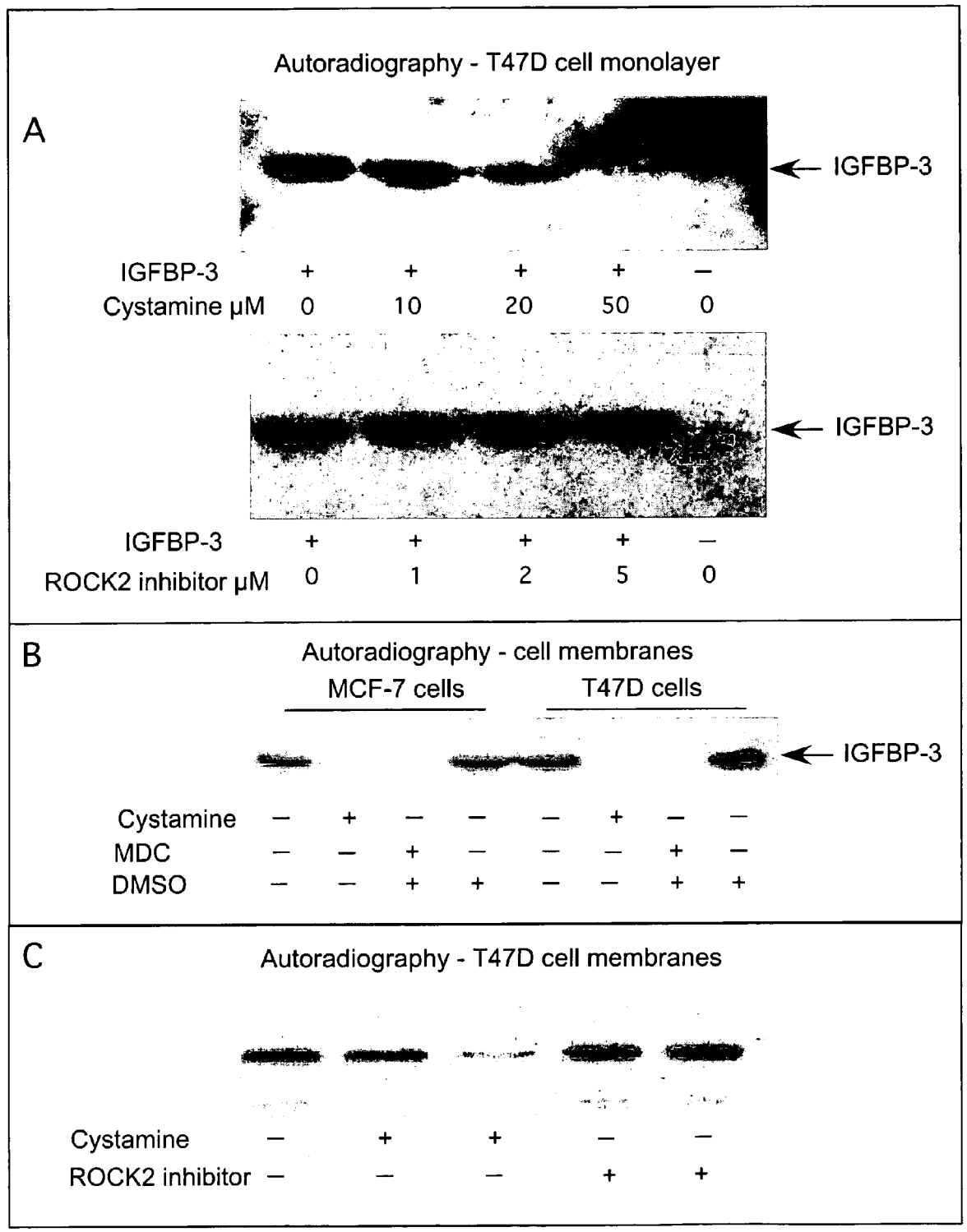
Fig. 2 Mishra & Murphy

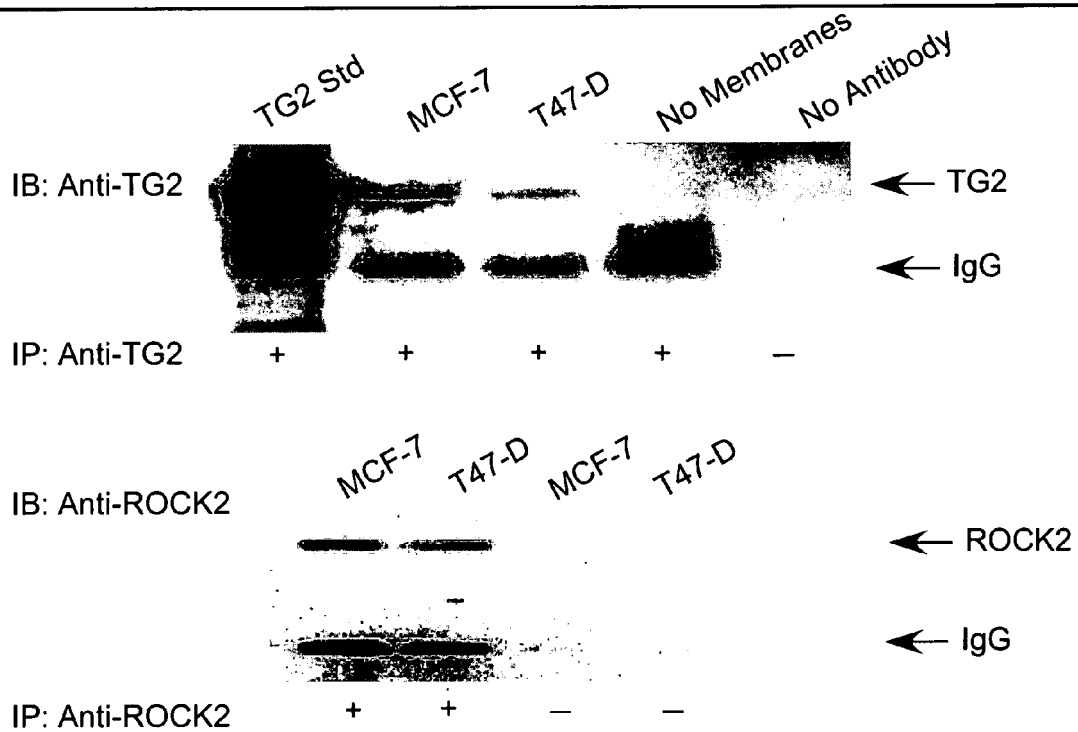
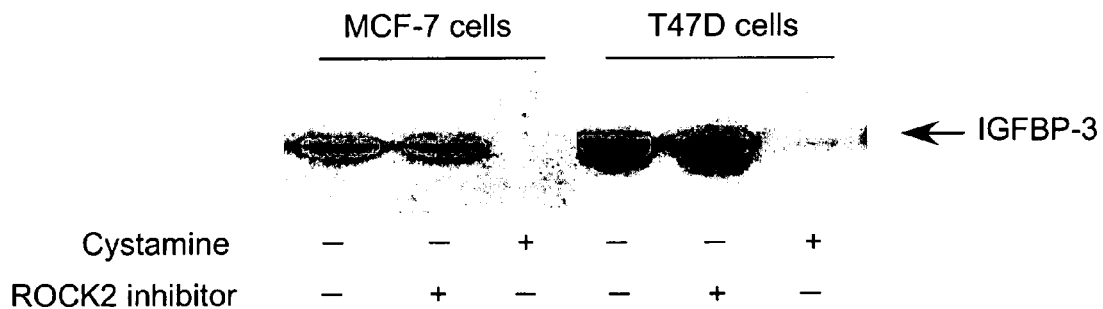
Fig. 3 Mishra & Murphy

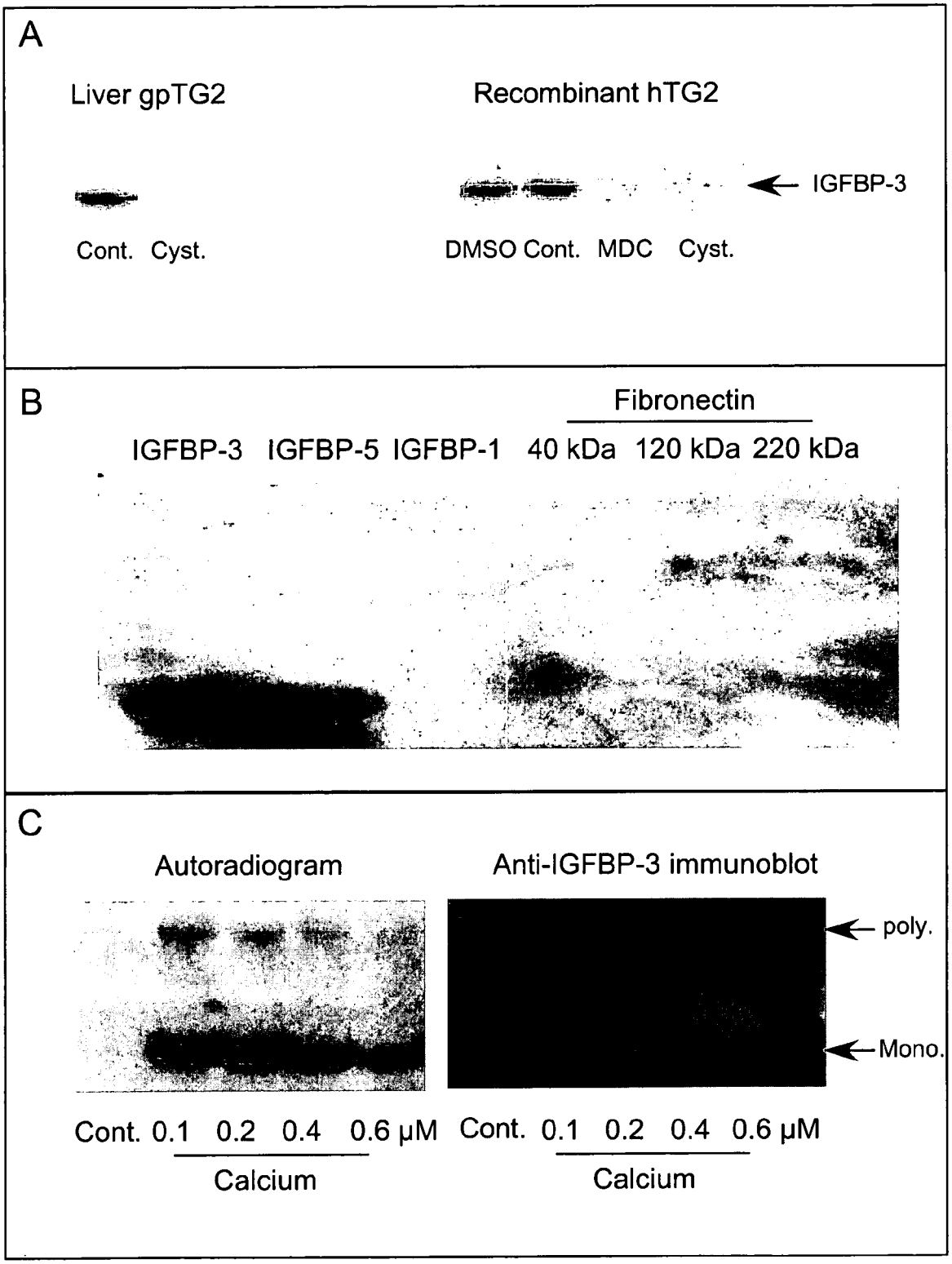
Fig. 4 Mishra & Murphy

Fig. 5 Phosphorylation of retinoblastoma protein and p53 oncoprotein by tissue transglutaminase
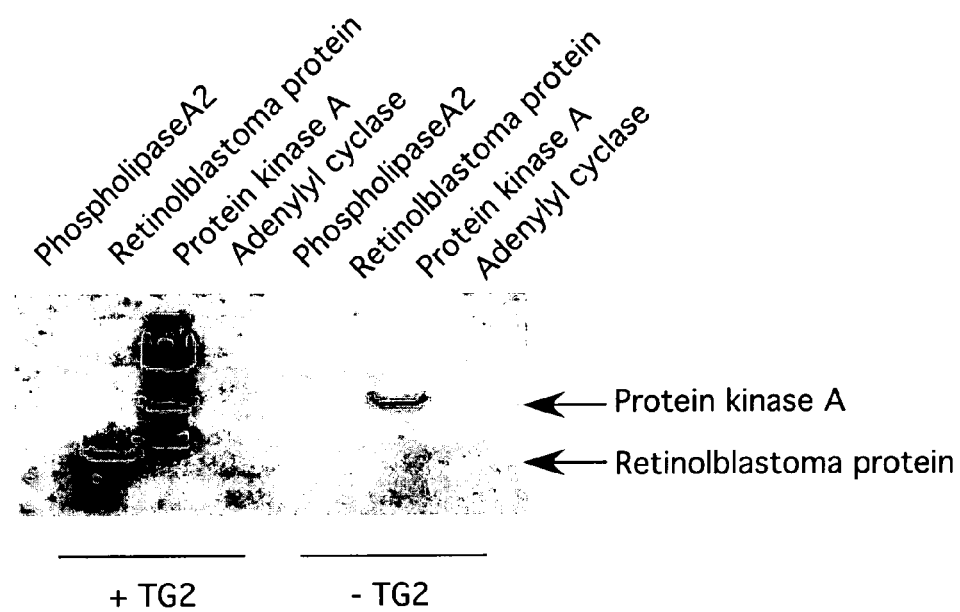
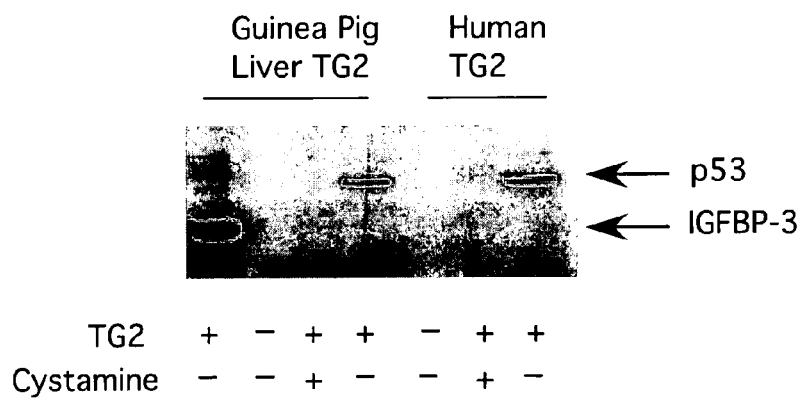

TRANSGLUTAMINASE HAS INTRINSIC KINASE ACTIVITY

PRIOR APPLICATION INFORMATION

This application claims priority under 35 USC § 119(e) to Provisional Patent Application Ser. No. 60/539,594 filed on Jan. 29, 2004.

FIELD OF THE INVENTION

The present invention relates generally to the field of biotechnology. More specifically, the present invention relates to the field of biochemical assays and pharmaceutical identification.

BACKGROUND OF THE INVENTION

During the investigation of the mechanism of actions of insulin-like growth factor binding protein-3 (IGFBP-3), we identified tissue transglutaminase (TG2) as the kinase responsible for the phosphorylation of IGFBP-3. IGFBP-3 is a multifunctional protein that not only functions to transport the insulin-like growth factors (IGF-I and IGF-II ) and modulate the actions of these growth factors but also has IGF-independent and anti-proliferative and proapoptotic effects (Jones and Clemmons, 1995, *Endoc. Rev.*, 16:3–34). It can both enhance and inhibit the effects of IGF-I in vivo and in vitro depending upon experimental conditions (De-Mellow and Baxter, 1988, *Biochem. Biophys. Res Commun.*, 156:199–204; Valentinis et al., 1996, *Mole. Endocrinol.*, 9:361–367; Oh et al., 1995, *Prog. Growth Factor Res.*, 6:205–212; Lalou et al., 1996, *Endocrinology* 137:3206–3212; Hong et al., 2002, *J. Biol. Chem.*, 277: 10489–10497).

In addition to these IGF-dependent effects, emerging evidence suggests that IGFBP-3 also functions directly to stimulate apoptosis (programmed cell death) and inhibits cellular proliferation of various cell lines including human breast cancer cells (Oh et al., 1995). However these IGF-independent effects are only apparent under conditions where the IGF-I dependent effects are not observed. For example, studies with mutant IGFBP-3 and IGFBP-3 fragments which have minimal affinity for IGF-I (Lalou et al., 1996; Hong et al., 2002) and with cell lines devoid of IGF-I receptors (Valentinis et al., 1996). We believe that phosphorylation has some role in the IGF-independent effects of IGFBP-3.

In an attempt to further understand the mechanisms that allow for these opposing effects of IGFBP-3 we have investigated the interaction of IGFBP-3 with breast cancer cell membranes. In addition to proteolysis we have recently reported that IGFBP-3 is phosphorylated by breast cancer cells by a process that occurs on the cell membranes, does not require internalization and is inhibited by IGF-I (Mishra and Murphy, 2003, *Endocrinology* 144:4042–4050). Phosphorylation of IGFBP-3 by this membrane-associated kinase enhanced the binding affinity of IGFBP-3 for IGF-I (Mishra and Murphy, 2003, *Endocrinology* 144:4042–4050). Thus phosphorylation of IGFBP-3 at the membrane favors the interaction of IGF-I with IGFBP-3 rather than the IGF-I receptor. Furthermore, since formation of IGF-I/IGFBP-3 complexes inhibits binding of IGFBP-3 to the cell membrane, phosphorylation of IGFBP-3 may modulate its proapoptotic anti-proliferative effects. To further understand the role of this kinase in physiological regulation of IGFBP-3 action we purified this kinase activity from T47D breast cancer cells. We subsequently demonstrated that this kinase activity is attributed to TG2.

Tissue transglutaminase (TG2) is a ubiquitous enzyme that is involved in post-translation modification and protein-protein interactions. It functions to cross-link glutamine residues with lysine residues resulting in protein polymerization, cross-linking of dissimilar proteins, and incorporation of diamines and polyamines into proteins. It has not previously been known to have kinase activity. In our recent report (Mishra and Murphy, 2003, *Endocrinology* 144:4042–4050) we demonstrated that insulin-like growth factor binding protein-3 (IGFBP-3) was phosphorylated by breast cancer cell membranes and that this activity was due to TG2. Antiserum to TG2 and protein A-sepharose were used to immunoprecipitate TG2 from IGFBP-3 affinity purified membrane fractions. The immunoprecipitates retained IGFBP-3 kinase activity whereas immunoprecipitation deleted kinase activity in the membrane supernatant. The inhibitors of TG2, cystamine and monodansyl cadaverine, abolished the ability of the T47D cell membrane preparation to phosphorylate IGFBP-3. Both TG2 purified from guinea pig liver and recombinant human TG2 expressed in insect cells were able to phosphorylate IGFBP-3 in vitro. TG2 kinase activity was inhibited in a concentration dependent fashion by calcium, which has previously been shown to be important for the cross-linking activity of TG2. These data provide compelling evidence that TG2 has intrinsic kinase activity, a function that has not previously been ascribed to TG2. Furthermore we provide evidence that TG2 is a major component of the IGFBP-3 kinase activity present on breast cancer cell membranes.

Although TG2 contains a GTP binding domain and can hydrolyse both GTP and ATP (Lai et al., 1998, *J. Biol. Chem.*, 273:1776–1781) it has not previously been reported to have kinase activity. It has however been reported to be involved in apoptosis (Thomazy & Davies, 1999 *Cell Death Differ.*, 6:146–154).

TG2 belongs to a family of nine evolutionary related genes that catalyze the posttranscriptional modification of proteins by inserting an isopeptide bond within or between polypeptide chains. None of the these transglutaminase family members have previously reported to have kinase activity. Although we initially demonstarted that the most abundant member of this family, namely TG2 has intrinsic kinase activity directed towards IGFBP-3 we have also shown that another member of the TG family, namely human coagulation factor XIIIa has kinase activity directed against IGFBP-3. This makes it a reasonable prediction that all members of the TG family have this kinase activity. Furthermore we have shown that the kinase activity of TG2 is not restricted to IGFBP-3 but other substrates as well. TG2 also phosphorylated the tumor suppressor genes p53 and retinoblastoma protein (pRb) and histone H3 (FIG. 5). These proteins have been shown to be critically important in cellular proliferation and disturbances in their expression and/or function is apparent in many cancers and disease states associated with increased cell proliferation.

Although the cross-linking activites of TG2 have been thought important in apoptosis this has not been definitively demonstrated. We have shown that the calcium, which stimulates the cross-linking activites of TG2 actually inhibits the kinase activity and therefore we propose that calcium acts as a switch to change the function of TG2 from a kinase to a cross-linking enzyme.

SUMMARY OF THE INVENTION

According to a first aspect of the invention, there is provided a method of identifying compounds capable of modulating TG2 kinase activity comprising: adding a test compound to a mixture comprising TG2 and a suitable TG2 kinase substrate, incubating the mixture under conditions promoting TG2 kinase activity, and determining if the test compound activates TG2 kinase activity as indicated by greater than expected TG2-mediated phosphorylation of the TG2 kinase substrate or inhibits TG2 kinase activity as indicated by lower than expected TG2-mediated phosphorylation of the TG2 kinase substrate as compared to a control comprising TG2 and a suitable TG2 kinase substrate.

According to a second aspect of the invention, there is provided a pharmaceutical composition comprising a compound identified as described above for treating diseases characterized by excessive cell proliferation and/or apoptosis.

BRIEF DESCRIPTION OF THE DRAWINGS

FIG. 1. Purification of IGFBP-3 kinase from T-47D cells and identification as transglutaminase. Solubilized membranes were chromatographed on Sephracryl S-100 (panel A) and fractions containing kinase activity (closed symbols) were pooled and analyzed on a High Q anion exchange column (panel B). The active fractions (38 to 43) were pooled and applied to an IGFBP-3 affinity column. The fractions from each purification step were analyzed by immunoblot using TG2 antiserum (panel C).

FIG. 2. The effect of TG2 and ROCK2 inhibitors on phosphorylation of IGFBP-3 by breast cancer cell monolayers (panel A) or cell membranes (Panel B and C). In panel A various concentrations of cystamine of the ROCK2 inhibitor, R-(+)trans-N-(4-pyridyl)-4-(laminoethyl)-cyclohexanecarboxamide dihydrochloride, were pre-incubated with T47D cell monolayers prior to determining the ability of the cell monolayer to phosphorylate IGFBP-3. In panel B, cystamine (20 µM), monodansyl cadaverine (MDC, 200 µM) or the vehicle DMSO (0.005%) was added to MCF-7 and T47D cell membranes and the ability of these membranes to phosphorylate IGFBP-3 was determined. In panel C, the ability cystamine (10 and 20 µM) and the ROCK2 inhibitor, R-(+)trans-N-(4-pyridyl)-4-(laminoethyl)-cyclohexanecarboxamide dihydrochloride (2 and 5 µM) to inhibit phosphorylation of IGFBP-3 by T47D cell membranes was compared.

FIG. 3. Immunodepletion and immunoprecipitation of IGFBP-3 kinase activity from T47D solubilized membranes. In panel A, solubilized T47D cell membranes were incubated with antibodies to TG2 or ROCK2. After the immunoprecipitates were pelleted using protein-A agarose, the supernatants were tested for the ability to phosphorylate IGFBP-3. In panel B TG2 and ROCK2 were immunoprecipitated from solubilized MCF-7 or T47D cell membranes and analyzed on SDS-PAGE. To demonstrate the presence of these two proteins in the immunoprecipitates, the membrane was immunoblotted with anti-TG2 or anti-ROCK2 antibodies. In panel C the presence of IGFBP-3 kinase activity in the anti-TG2 immunoprecipitates was demonstrated and ability of cystamine (20 µM) and the ROCK2 inhibitor (5 µM) to inhibit this kinase activity was assessed FIG. 4. Purified guinea pig (pg) liver TG2 and recombinant human TG2 have IGFBP-3 kinase activity. In panel A, the effect of cystamine (cyst, 20 µM) and MDC (200 µM) on the IGFBP-3 kinase activity of Guinea pig and recombinant TG2 was examined and compared to controls (cont.) or vehicle only (DMSO, 0.005%). In panel B, the ability of recombinant human TG2 to phosphorylate IGFBP-1, IGFBP-5, fibronectin and fibronectin fragments was investigated. In panel C, the effect of calcium on recombinant TG2 kinase activity and cross-linking activity was investigated.

FIG. 5. Retinoblastoma protein, p53 and histone H3 are substrate for the tissue transglutaminase kinase activity. Recombinant tissue transglutaminase was used to phosphorylate IGFBP-3, retinoblastoma proteins, p53 and histone H3 in vitro. The phosphorylated proteins were resolved electrophoresis on a polyacrylamide gel and visualized by autoradiography.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, the term "treating" in its various grammatical forms refers to preventing, curing, reversing, attenuating, alleviating, minimizing, suppressing or halting the deleterious effects of a disease state, disease progression, disease causitive agent other abnormal condition.

As used herein, "effective amount" refers to the administration of an amount of a given compound that achieves the desired effect.

As used herein, "TG" refers to any of a variety of transglutaminases. Herein, TG2, or tissue transglutaminase, is the exemplary transglutaminase. Other suitable transglutaminases may also be used, for example, but by no means limited to, human factor XIIIa (hFXIIIa), transglutaminse-1, transglutaminse-2, transglutaminase-3, transglutaminse-4, transglutaminse-5, transglutaminse-6, transglutaminse-7 and epb42.

As used herein, "TG kinase substrate" refers to proteins, fragments thereof or peptides that are phosphorylated by TG kinase activity. Examples include but are by no means limited to IGFBP-3, IGFBP-5, p52 tumor suppressor gene, retinoblastoma protein and histone H3.

In one aspect of the invention, there is provided a method of identifying compounds capable of modulating TG kinase activity comprising: adding a test compound to a mixture comprising TG and a suitable TG kinase substrate, incubating the mixture under conditions promoting TG kinase activity, and determining if the test compound activates or modulates TG kinase activity as indicated by greater than expected TG-mediated phosphorylation of the TG kinase substrate or if the test compound inhibits TG kinase activity as indicated by lower than expected TG-mediated phosphorylation of the TG kinase substrate as compared to a control comprising TG and a suitable TG kinase substrate incubated under conditions promoting TG kinase activity.

As will be apparent to one of skill in the art, other suitable kinase assays known in the art may be used within the invention and these assays may be modified such that they may be used for high throughput assays.

Since regulation of p53 and pRb activity is critical to cell cycle control and unregulated p53 and pRb activity is the hallmark of many cancerous cells, identification of TG kinase modulators may have potential benefit in the treatment of disease states. Phosphorylation of p53 and pRb plays a very important role in the interaction of these two proteins with other proteins involved in regulation of cell cycle progression and apoptosis. Phosphorylation of these two proteins (p53 and pRb) by TG may be relevant to the role of TG in cell proliferation and/or apoptosis. Therefore, it is likely that modulation of kinase activity of TG2 or related TG family member could be used in the treatment of diseases characterized by cell proliferation and/or apoptosis.

As will be appreciated by one of skill in the art, compounds identified as useful in modulating transglutaminase activity using one of the above-described methods or, as discussed below, pharmaceutical compositions prepared therefrom, may be useful in treating or preventing diseases characterized by cell proliferation, for example but by no means limited to various forms of cancer, including but not limited to breast, prostate and colon cancer, or diseases characterized by impaired apoptosis, for example, but by no means limited to psoriasis, and chronic leukemias.

It is of note that the pharmaceutical compositions may be combined with other components known in the art, for example, targeting molecules or permeation enhancers, or may be combined with other treatments known in the art.

As will be appreciated by one of skill in the art, the test compound or test agent may comprise a small molecule, chemical compound, peptide, antibody or antibody fragment or other such compound.

The invention is also directed to compounds isolated by these methods and the use thereof to prepare pharmaceutical compositions. In these embodiments, the test compound may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, *Remington: The Science and Practice of Pharmacy*, 2000, Gennaro, AR ed., Eaton, Pa.: Mack Publishing Co.

As will be apparent to one knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

The invention will now be described by way of examples. However, the examples are for illustrative purposes and the invention is not in any way limited by the examples.

Biotinylation of IGFBP-3

Non-glycosylated *E. coli* derived IGFBP-3 was biotinylated using p-biotinoyl-aminocaproic acid-N-hydroxy-succinamide ester (Roche Molecular Biochemicals, Mannheim, Germany) as previously described (Mishra and Murphy, 2003).

Purification of IGFBP-3 Kinase Activity

Solubilized T47D cell membranes were prepared using membrane preparation kit (Pierce, Rockford, Ill.) according to the manufacturer's instructions in the presence of protease inhibitors (0.1 mM PMSF, 10 mM aprotinin and 10 µg/ml leupeptin). 3 ml of solubilized membranes was filtered through 0.22 µm filter and loaded on 16/60 Sephacryl S-100 gel filtration column which had been equilibrated with 20 mM Tris/HCl, 0.02% $NaN_3$, and pH 7.5. The eluate was monitored for absorbance at 280 nm through a Pharmacia UV-1 single path monitor. 1 ml fractions were collected at a flow rate of 1 ml/min and stored at −70° C. The activity was consistently found in fractions within molecular weight range of 65 to 85 kDa. A 20 µl aliquot of each fraction was assayed for IGFBP-3 kinase activities. Active fractions were pooled and concentrated with Amicon Centricon 30 filter. Buffer-exchanged sample was passed through High Q anion exchange column (Bio-Rad, CA) which had been equilibrated with 50 mM Tris/HCl pH 8.0 containing 0.05 M NaCl, 0.02% $NaN_3$. Separation was performed in a linear gradient from 0.05 to 0.5 M NaCl over 50 min at flow rate of 1 ml/min and 1 ml fractions were collected. Fractions containing kinase activity were concentrated using Amicon Centricon filter, desalted and buffer was exchanged using Micro Bio-Spin chromatography columns (BioRad, CA) and loaded on to an IGFBP-3-Sepharose 4B affinity column (2 ml bed volume). Bound proteins were first eluded with 0.05 M sodium phosphate containing 0.15 M NaCl (pH 7.2) followed by 0.1 M acetate buffer containing 0.5M NaCl (pH 4.0). Eluted fractions were desalted, concentrated and used for IGFBP-3 kinase assay. Fraction with IGFBP-3 kinase activity was processed for liquid chromatography mass spectroscopy (LC-MS).

For LC-MC analysis, 100 µl of desalted affinity fraction was digested with sequencing grade trypsin. The peptide mixture was lyophilized and resuspended in 10 µl of 0.05% TFA and used for pHPLC-MALDI-QqTOF analysis. Chromatographic separation was performed using an Agilent 1100 Series system. Sample (5 µl) were injected into 150 µm×150 mm column (Vydac 218 TP C18, 5 µ) and eluted with 1–80% acetonitrile (0.1% TFA) in 60 min. Major ion peaks of the total ion chromatogram were analyzed by mass spectrometry (MS) in Manitoba/Sciex prototype quadrupole/time of flight mass spectrometer. In this instrument ions are produced by irradiation of the target using proton pulses from a 20-Hz nitrogen laser and the mass accuracy is within a few mDa in TOF spectra. Identification of the tryptic peptides was done by searching database against the peptide fingerprints using Mascot search engine (http://www.matrix-science.com)

Phosphorylation of IGFBP-3

Polystyrene tube were coated with streptavidin and blocked with bovine serum albumin, washed in saline and stored at −20° C. until used. Biotinylated IGFBP-3 (500 ng) was added in streptavidin-coated tubes for 2 h on ice. At the end of incubation, excess, unbound IGFBP-3 was removed.

Tubes were placed on ice and phosphorylation reaction mixture containing 20 mM Tris buffered saline pH 7.5, 10 mM Mg/ATP, 60 µCi/ml $^{32}$P-ATP was added. Reaction was initiated by the addition of membrane fraction and allowed to proceed for 30 min at 30° C. Reaction was stopped by addition of SDS-PAGE sample buffer, boiled for 7–10 min and analyzed on 11% gel. Subsequently gels were dried and processed for autoradiography. In some cases 2 µU of pure TG2 (Sigma-Aldrich, MO) or histidine-tagged full length human TG2 expressed using baculovirus expression system in insect cells and purified by Ni(II)-nitroacetate agarose chromatography was used to phosphorylate IGFBP-3 in presence or absence of TG2 specific inhibitors. In experiments where cell monolayers were used to phosphorylate IGFBP-3, cells were grown in 24-well culture plate to near confluence and washed with PBS to remove residual media and serum. Phosphorylation was then performed in 100 pl reaction mixture as above, containing 1 µg IGFBP-3 for 10 min at 37° C. At the end of incubation, reaction mixture was aspirated, reaction was stopped by addition of sample buffer and analyzed on 11% gel. In some experiments, cell monolayer were treated with TG2 inhibitor for 30 min prior to the phosphorylation reaction.

Immunoprecipitation

To 200 µl of solubilized membranes from T47D of MCF-7 cells, 10 µl of anti-TG2 goat polyclonal antiserum (Upstate Biotechnology, Lake Placid, N.Y.) and incubated for 1 h at 4° C. 20 µl of protein A-agarose (Pierce) was added and further incubated on a rotating device overnight at 4° C. At the end of incubation the pellet was washed four times in ice cold PBS. The supernatant was discarded and the pellet was resuspended in 50 µl of kinase buffer. 10 µl of the resuspended sample was used for phosphorylation of 500 ng of IGFBP-3. The samples were analyzed by SDS-PAGE, autoradiography and immunoblotting with TG2 antiserum.

Western Blotting

Various column fractions that had IGFBP-3 kinase activity were analyzed on 10% SDS-PAGE gel and transferred to nitrocellulose membrane. Membranes were blocked in 5% milk, incubated with TG2 antiserum diluted to 1:1000, washed three times, (5 min each) in TBST (10 mM Tris/HCl, 150 mM NaCl, 0.05% Tween-20, pH 8.0) and incubated with HRP-conjugated anti-goat (Santa Cruz Biotechnology, Calif.) secondary antibody (1:3000 dilution) for 1 h at room temperature. Membranes were washed three times in TBST and subsequently analyzed with ECL.

Purification of IGFBP-3 Kinase Activity from T-47D Cell Membranes

The IGFBP-3 kinase activity was purified from solubilized T-47D cell membranes using immobilized biotinylated IGFBP-3 as a substrate. A three step procedure was used involving gel permeation, ion exchange and IGFBP-3 affinity chromatography (FIG. 1). Fractions eluted from the IGFBP-3 affinity column under acidic conditions which contained IGFBP-3 kinase activity were further analyzed by HPLC and tandem mass spectroscopy. Using the Mascot search engine a variety of proteins were identified which had significant scores (Table 1). Of these, TG2 had the highest score and there was wide coverage over the entire TG2 molecule with peptides from various regions of the molecule identified. Tandem mass spectroscopy was used to confirm the sequence of various peptide fragments (Table 2).

Fractions containing peak IGFBP-3 kinase activity from the various purification steps were analyzed by immunoblot using TG2 antiserum. Immunoreactive TG2 was present in all three samples (FIG. 1C). ROCK2 was also detectable in T47D cell membrane fractions.

We assessed the effect of the TG2 and ROCK2 inhibitors on phosphorylation of IGFBP-3 by cell monolayers. We have previously shown that intact washed cells were able to phosphorylate IGFBP-3 immobilized on polystyrene tubes (Mishra and Murphy, 2003). T47D cell monolayers were incubated for 30 minutes in the presence of various concentrations of cystamine, an inhibitor of TG2. The washed cell monolayers were incubated with IGFBP-3 in the presence of $^{32}$P-ATP for 10 minutes at 37° C. After termination of the incubation, the IGFBP-3 was analyzed by SDS-PAGE and autoradiography (FIG. 2A). Inhibition was seen with as little as 20 µM and complete inhibition was apparent with 50 µM of cystamine. Similar experiments were undertaken utilizing membrane preparations from both T47D and MCF-7 cells. As reported previously both T47D and MCF-7 cells were able to phosphorylate IGFBP-3. This process was inhibited by cystamine and MDC in both cells lines (FIG. 2B). DMSO the vehicle in which MDC was dissolved had no effect. Since TG2 has been found in association with ROCK2, a Rho-kinase (Singh et al., 2001, *EMBO J.*, 20:2413–2423), and ROCK2 was present in the affinity purified cell membrane fractions, we investigated the effect of the ROCK2 inhibitor, R (+)trans-N-(4-pyridyl)-4-(1aminoethyl)-cyclohexanecarboxamide dihydrochloride. The ROCK2 inhibitor had no effect on IGFBP-3 phosphorylation (FIG. 2C).

We next examined the effect of TG2 and ROCK2 antisera on IGFBP-3 kinase activity present in cell membrane preparations. Antiserum against TG2 but not ROCK2 antiserum was able to immunodeplete IGFBP-3 kinase activity from membrane preparations (FIG. 3A). When the immunoprecipitates were analyzed for kinase activity, the precipitates obtained with TG2 antiserum but not those obtained with ROCK2 antiserum had kinase activity. Furthermore, the IGFBP-3 kinase activity present in the immunoprecipitates was inhibited by cystamine but not by the ROCK2 inhibitor.

Purified guinea pig liver TG2 and human recombinant TG2 both were able to phosphorylate IGFBP-3 (FIG. 4A). This process was inhibited cystamine and MDC. The related binding protein IGFBP-5 was also phosphorylated by TG2 whereas IGFBP-1 was not phosphorylated by TG2 (FIG. 4B). Consistent with a previous report (Sakai et al., 2001, *J. Biol. Chem.*, 276:8740–8745), an increase in the molecular mass of IGFBP-1 was observed suggesting that TG2 can polymerase IGFBP-1. Fibronectin, another reported substrate for TG2 (Akimov and Belkin, 2001, *J. Cell Sci.*, 114:2989–3000), was not phosphorylated by this enzyme under the conditions we used to phosphorylate IGFBP-3 (FIG. 4B). Since calcium is necessary for the cross linking activity of TG2 (Kang et al., 2002, *Biochem. Biophys. Res. Commun.*, 293:383–390), we examined the effect of increasing concentration of calcium on the kinase activity of TG2. As the calcium concentration was increased we observed a decrease in the kinase activity of TG2. Concomitantly there was an increase in polymerization of IGFBP-3 observed (FIG. 4C).

Analysis of purified fractions from breast cancer cells containing IGFBP-3 kinase activity identified a number of potentially interesting proteins. Of these only ROCK2 was previously known to have kinase activity and we assumed that this was responsible for phosphorylation of IGFBP-3. However a specific inhibitor of ROCK2 kinase activity had no effect on the IGFBP-3 kinase activity of breast cancer cell monolayers or purified membrane preparations. Furthermore, immunoprecipitation of ROCK2 from membrane preparation did not deplete the IGFBP-3 kinase activity whereas this activity could be completely removed by immunoprecipitation with TG2 antiserum. These data, together with the demonstration that both guinea pig liver TG2 and recombinant human TG2 could phosphorylate IGFBP-3 provided convincing evidence that TG2 can function as ectokinase in breast cancer cells. Furthermore it appears to account for virtually all the IGFBP-3 kinase activity present on the membrane of these cells since very little residual activity was apparent after immunoprecipitation of TG2 from breast cancer membrane preparations. We have previously shown that IGFBP-3 can also be phosphorylated by an ecto-kinase present on COS cells (Mishra and Murphy, 2003) and human umbilical vein endothelail cells. The latter is particularly relevant since endothelial cells are know to express high levels of TG2 on their plasma membranes (Fesus and Piacentini, 2002, Trends Biochem. Sci., 27:534–539).

TG2 is a ubiquitous enzyme that has been implicated in a variety of biological processes. It is important in post-translational protein modification and protein-protein interactions. It functions as a calcium-dependent transamidating acytransferase that crosslinks glutamine residues with lysine residues in the same proteins resulting in polymerization or with lysine residues in other proteins resulting in protein cross-linking (Fesus and Piacentini, 2002). In addition to adding diamines and polyamines to proteins it can also deamidate glutamine residues to glutamic acid which introduces a negative charges and changes the pI of the protein. Recently it has been reported to also function as a protein disulfide isomerase (Hassegawa et al., 2003, Biochem. J., 373:793–803). However this latter function unlike other functions described for TG2 was not calcium dependent and was not inhibited by GTP. TG2 has also been reported to function as novel G protein couple membrane receptor (Nakaoka et al., 1994, Science 264:1593–1596) and has been shown to have a role in transmitting signals from classical seven-transmembrane helix G-coupled receptors such as the $b_{1B}$-adrenergic receptor (Chen et al., 1996, J. Biol. Chem., 271, 32385–32391). Here we report that TG2 has another novel enzymatic function namely kinase activity. It is likely to phosphorylate a variety of other proteins.

Interestingly the kinase activity of TG2 was inhibited by increasing calcium and consistent with previous reports (Kang et al., 2002) increasing the calcium concentration enhanced the cross-linking activity of TG2. In the case of TG2 activity directed against IGFBP-3, calcium appeared to act as switch, inhibiting kinase activity and enhancing cross-linking activity.

TG2 has been implicated in a variety of processes where phosphorylation is important. These include activation of RhoA and M kinase pathways (Singh et al., 2003, J. Biol. Chem. 278:391–399), activation of CREB (Tucholski and Johnson, 2003, J. Biol. Chem., 278:26838–26843) and activation of phospholipase C (Nakaoka et al., 1994).

In most cell types TG2 is predominantly localized in the cytoplasm and the nucleus (Fesus and Piacentini, 2002) but it is also localized to the cell membrane (Gaudry et al., 1999, J. Biol. Chem., 274:30707–30714). It ca be released from various cell types under certain circumstances such as inflammation and during apoptotic cell death (Griffin and Verderio, 2000, in Tissue transglutaminase in cell death in programmed Cell Death in Animals and Plants, eds. Bryant, J. A., Hughes, S. G. & Garland, J. M. (BIOS Scientific Publishers Ltd. Oxford), pp. 223–240). In the latter case it appears to be important in the latter stages of the process and may function to prepare dying cells for phagocytosis by macrophages (Griffin and Verderio, 2000, in Tissue transglutaminase in cell death in programmed Cell Death in Animals and Plants, eds. Bryant, J. A., Hughes, S. G. & Garland, J. M. (BIOS Scientific Publishers Ltd. Oxford), pp. 223–240). However, TG2 gene expression is activated early in apoptosis, particularly morphogenic apoptosis, in developing embryonic limbs (Thomazy and Davies, 1999, Cell Death Differ., 6:146–154) and retinoid-induced apoptosis (Kochhar et al., 1993, Prog. Clin. Biol. Res., 383B, 815–825).

Interestingly, IGFBP-3 has been shown to be pro-apoptotic in a variety of cell lines (Oh et al., 1995; Hong et al., 2002; Longobardi et al., 2003, Endocrinology 144:1695–1702). This process is thought to be an IGF-independent effect of IGFBP-3 mediated by binding of IGFBP-3 to a surface receptor (Oh et al., 1993, J. Biol. Chem. 268: 26045–26048). The presence of IGF-I inhibits the interaction of IGFBP-3 with binding sites present on breast cancer cells (Yamanaka et al., 1999, Endocrinology 140:1319–1328) and thus would potentially inhibit the pro-apoptotic IGF-independent effects of IGFBP-3. We have previously shown that phosphorylation of IGFBP-3 by TG2 enhances the affinity of this binding protein for IGF-I. Thus phosphorylation of IGFBP-3 by TG2 could serve to attenuate the pro-apoptotic effects of IGFBP-3 and the proliferative effect of IGF-I by enhancing formations of IGFBP-3/IGF-I binary complexes and reducing the interaction of IGF-I and IGFBP-3 with their cognate membrane binding sites.

In summary we have identified a novel kinase function for TG2. We provide compelling evidence that TG2 is the major IGFBP-3 kinase present on breast cancer cell membranes. The observation that TG2 has kinase activity should serve as a stimulus to re-examine the role of the TG2 kinase activity in other biological processes where TG2 kinase activity could be important.

While the preferred embodiments of the invention have been described above, it will be recognized and understood that various modifications may be made therein, and the appended claims are intended to cover all such modifications which may fall within the spirit and scope of the invention.

TABLE 1

Proteins whose tryptic peptide fragments were identified by HPLC/tandem spectroscopy in IGFBP-3 affinity column fraction containing kinase activity.

| Protein | Score* | Accession number |
|---|---|---|
| Transglutaminase | 50 | P21980 |
| ROCK2 | 48 | NP-004841 |
| WW domain containing adaptor isoform I | 37 | NP-057712 |
| Glutamate receptor | 36 | AAD15616 |
| G protein coupled receptor GPR 44 | 35 | AAD21055 |
| KIAA0322 | 33 | BAA20780 |

*Score determined as −10Log(P), where P is the probability that the observed match is a random event. A score >40 indicates indentity or extensive homology, p < 0.05.

TABLE 2

Transglutaminase peptide fragment identified by tandem mass spectroscopy in IGFBP-3 affinity column fraction containing kinase activity.

| TG2 residues | Sequence |
|---|---|
| 31–35 | LVVRR |
| 223–240 | VWSGMVNCNDDQGVLLGR |
| 422–433 | VGLKISTKSVGR |
| 553–562 | DCLTESNLIK |

The invention claimed is:

1. A method of identifying an agent capable of modulating Tissue Transglutaminase (TG2) kinase activity comprising: adding a test agent to a mixture comprising TG2 and a suitable TG2 kinase substrate, incubating the mixture under conditions promoting TG2 kinase activity, and determining if the test agent 1) activates TG2 kinase activity as indicated by a TG2 mediated phosphorylation of the TG2 kinase substrate wherein said activity is greater than TG2 mediated phosphorylation of TG2 kinase substrate control or 2) inhibits TG2 kinase activity as indicated by a lower TG2-mediated phosphorylation of the TG2 kinase substrate as compared to a control.

* * * * *